(12) United States Patent
Himmler et al.

(10) Patent No.: US 6,664,268 B1
(45) Date of Patent: Dec. 16, 2003

(54) CRYSTAL MODIFICATION B OF 8-CYANO-1-CYCLOPROPYL-7-(1S,6S-2,8-DIAZABICYCLO[4.3.0]NONAN-8-YL)-6-FLUORO-1,4-DIHYDRO-4-OXO-3-QUINOLINECARBOXYLIC ACID

(75) Inventors: Thomas Himmler, Odenthal (DE); Werner Hallenbach, Monheim (DE); Hubert Rast, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/856,670

(22) PCT Filed: Nov. 15, 1999

(86) PCT No.: PCT/EP99/08776

§ 371 (c)(1), (2), (4) Date: May 23, 2001

(87) PCT Pub. No.: WO00/31076

PCT Pub. Date: Jun. 2, 2000

(30) Foreign Application Priority Data

Nov. 25, 1998 (DE) .......................... 198 54 355

(51) Int. Cl.[7] ...................... A61K 31/4709; A61P 31/04; C07D 471/04
(52) U.S. Cl. .................. 514/300; 546/113; 546/156
(58) Field of Search ................ 514/300; 546/300; 546/113

(56) References Cited

U.S. PATENT DOCUMENTS 6,278,013 B1 * 8/2001 Bartel .................. 558/415

FOREIGN PATENT DOCUMENTS

| WO | 96/16055 | 5/1996 |
|---|---|---|
| WO | 97/31001 | 8/1997 |
| WO | 00/31075 | 6/2000 |
| WO | 00/52009 | 9/2000 |
| WO | 00/52010 | 9/2000 |

* cited by examiner

Primary Examiner—Evelyn Mei Huang
(74) Attorney, Agent, or Firm—Susan M. Pellegrino

(57) ABSTRACT

The present invention relates to a defined crystal modification of 8-cyano-1-cyclopropyl-7-(1S,6S-2,8-diazabicyclo[4.3.0]nonan-8-yl)-6-fluoro-1,4-dihydro-4-oxo-3-quinolinecarboxylic acid of the formula (I), to processes for its preparation and to its use in pharmaceutical preparations.

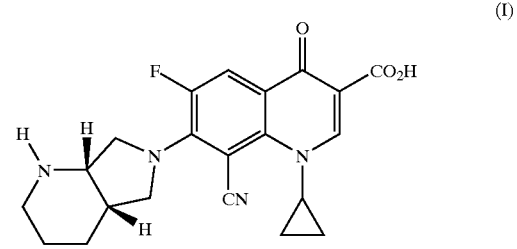

(I)

The crystal modification can be distinguished from other crystal modifications of 8-cyano-1-cyclopropyl-7-(1S,6S-2,8-diazabicyclo[4.3.0]nonan-8-yl)-6-fluoro-1,4-dihydro-4-oxo-3-quinolinecarboxylic acid of the formula (I) by its characteristic X-ray powder diffractogram and its differential thermodiagram (see description).

9 Claims, 4 Drawing Sheets

CRYSTAL MODIFICATION B OF 8-CYANO-1-CYCLOPROPYL-7-(1S,6S-2,8-DIAZABICYCLO[4.3.0]NONAN-8-YL)-6-FLUORO-1,4-DIHYDRO-4-OXO-3-QUINOLINECARBOXYLIC ACID

This application is the 371 of PCT/EP99/08776, filed on Nov. 15, 1999.

The present invention relates to a defined crystal modification of 8-cyano-1-cyclopropyl-7-(1S,6S-2,8-diazabicyclo[4.3.0]nonan-8-yl)-6-fluoro- 1,4-dihydro-4-oxo-3-quinolinecarboxylic acid, to processes for its preparation and to its use in pharmaceutical preparations.

Hereinbelow, 8-cyano-1-cyclopropyl-7-(1 S,6S-2,8-diazabicyclo[4.3.0]nonan-8-yl)-6-fluoro-1,4-dihydro-4-oxo-3-quinolinecarboxylic acid of the formula (I) is referred to as CCDC.

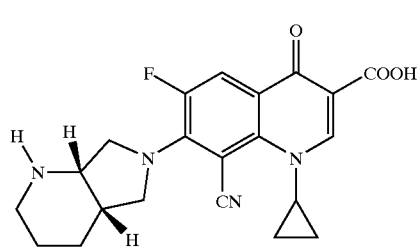

(I)

CCDC is known from DE-A 19 633 805 or PCT Appl. No. 97 903 260.4. According to these publications, it is prepared by reacting 7-chloro-8-cyano-1-cyclopropyl-6-fluoro-1,4-dihydro-4-oxo-3-quinolinecarboxylic acid with (1S,6S)-2,8-diaza-bicyclo[4.3.0]nonane in a mixture of dimethylformamide and acetonitrile in the presence of an auxiliary base. Water is added to the mixture and CCDC is then extracted from water using dichloromethane and is isolated by removing the extractant. This gives a powder whose crystal modification is not unambiguous. On the contrary, the powder is largely amorphous and can contain mixtures of different crystal modifications. If, by chance, a uniform crystal modification is formed, it is not clear how it can be extracted and obtained in a defined form. However, it is the precondition for preparing medicaments that, for an active compound which can be present in different crystal modifications, it can be stated unambiguously which of its crystal modifications is used for preparing the medicament.

The partially amorphous powder which is obtained by the preparation process outlined above is furthermore hygroscopic. However, amorphous solids, and in particular hygroscopic solids, are difficult to handle when being processed pharmaceutically since, for example, they have low bulk densities and unsatisfactory flow properties. Moreover, the handling of hygroscopic solids requires special work techniques and apparatuses to obtain reproducible results, for example with respect to the active compound content or the stability of the solid formulations produced.

It is therefore an object of the invention to prepare a crystalline form of a defined modification of CCDC which, owing to its physical properties, in particular its crystal properties and its behaviour towards water, is easy to handle in pharmaceutical formulations.

This object is achieved according to the invention by a novel crystalline form of CCDC which is referred to as modification B hereinbelow.

The invention accordingly provides the crystalline modification B of CCDC which is characterized in that it has an X-ray powder diffractogram with the reflection signals (2 theta) of high and medium intensity (>30% relative intensity) listed in Table 1 below.

TABLE 1

X-ray powder diffractogram of CCDC of the modification B
2θ (2 theta)

| |
|---|
| 8.91 |
| 13.23 |
| 14.26 |
| 14.40 |
| 15.34 |
| 17.88 |
| 19.70 |
| 20.78 |
| 21.86 |
| 28.13 |
| 30.20 |

BRIEF DESCRIPTION OF THE DRAWINGS

The X-ray powder diffractogram of the modification B is shown in FIG. 1. A differential thermodiagram characteristic of the modification B is shown in FIG. 2.

An infrared spectrum, measured in KBr of CCDC of the modification B is shown in FIG. 3.

Figure 4:
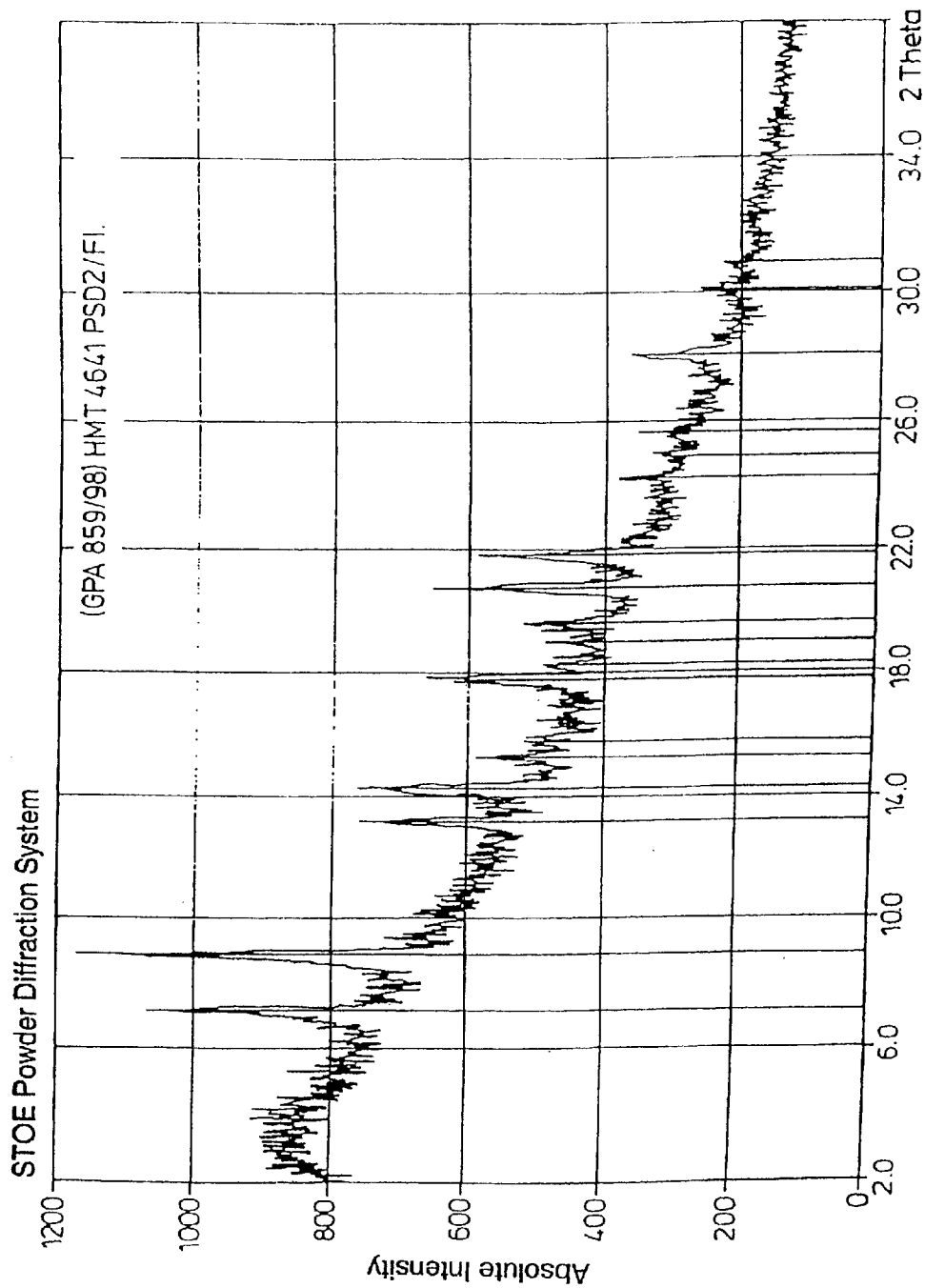

X-ray powder diffractogram of a light-brown solid obtained by the procedure of Comparative Example, at page 8 of the specification is shown in FIG. 4.

Moreover, the CCDC modification B according to the invention differs from other forms of CCDC in a number of further properties. These properties, on their own or together with the other parameters, may also serve for characterizing the CCDC modification B according to the invention.

Figure 2:
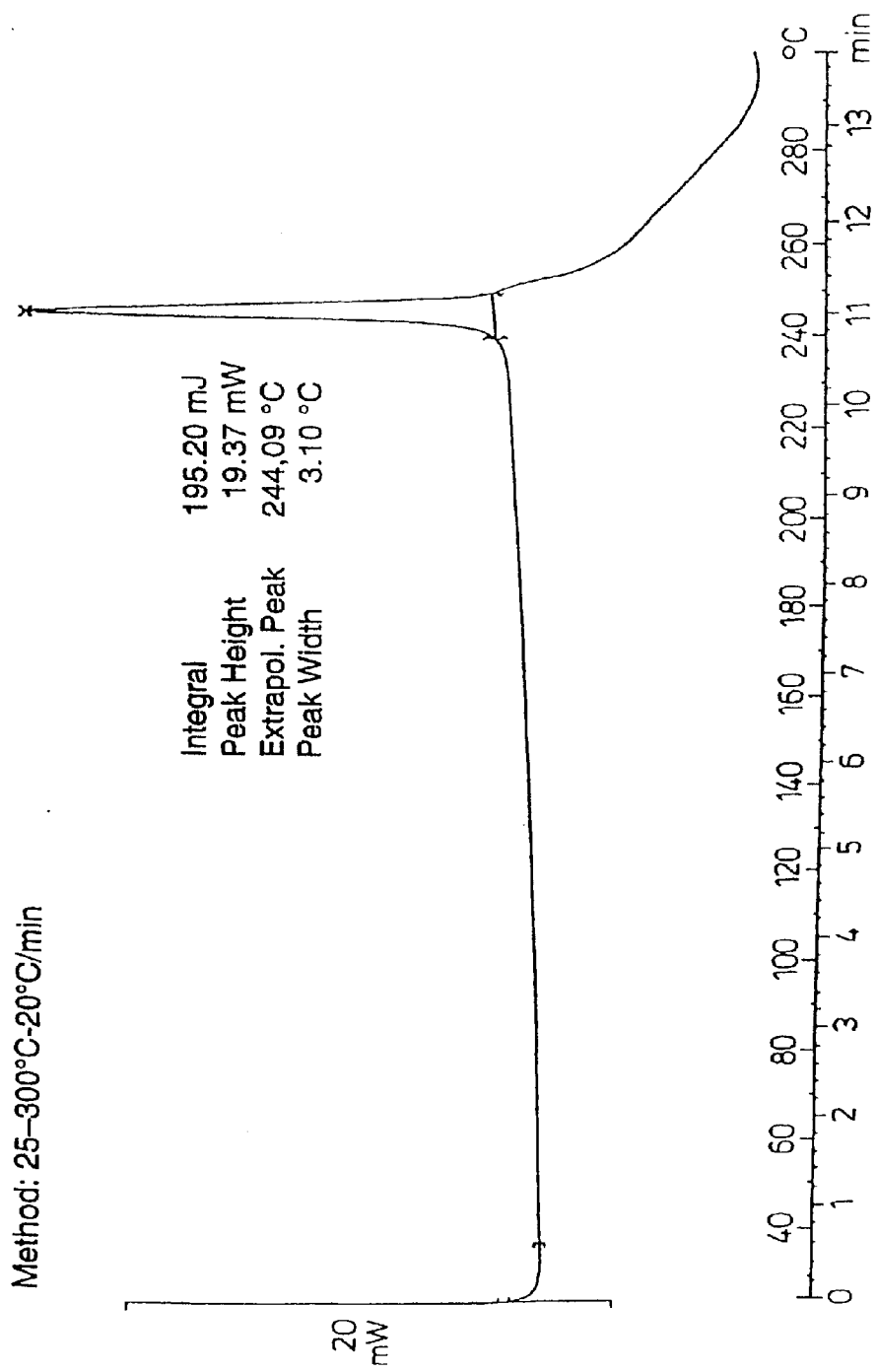

CCDC of the modification B is characterized by a melting point, determined with the aid of differential thermoanalysis (DTA), of from 243° C. to 245° C. A characteristic differential thermodiagram is shown in FIG. 2.

Figure 3:
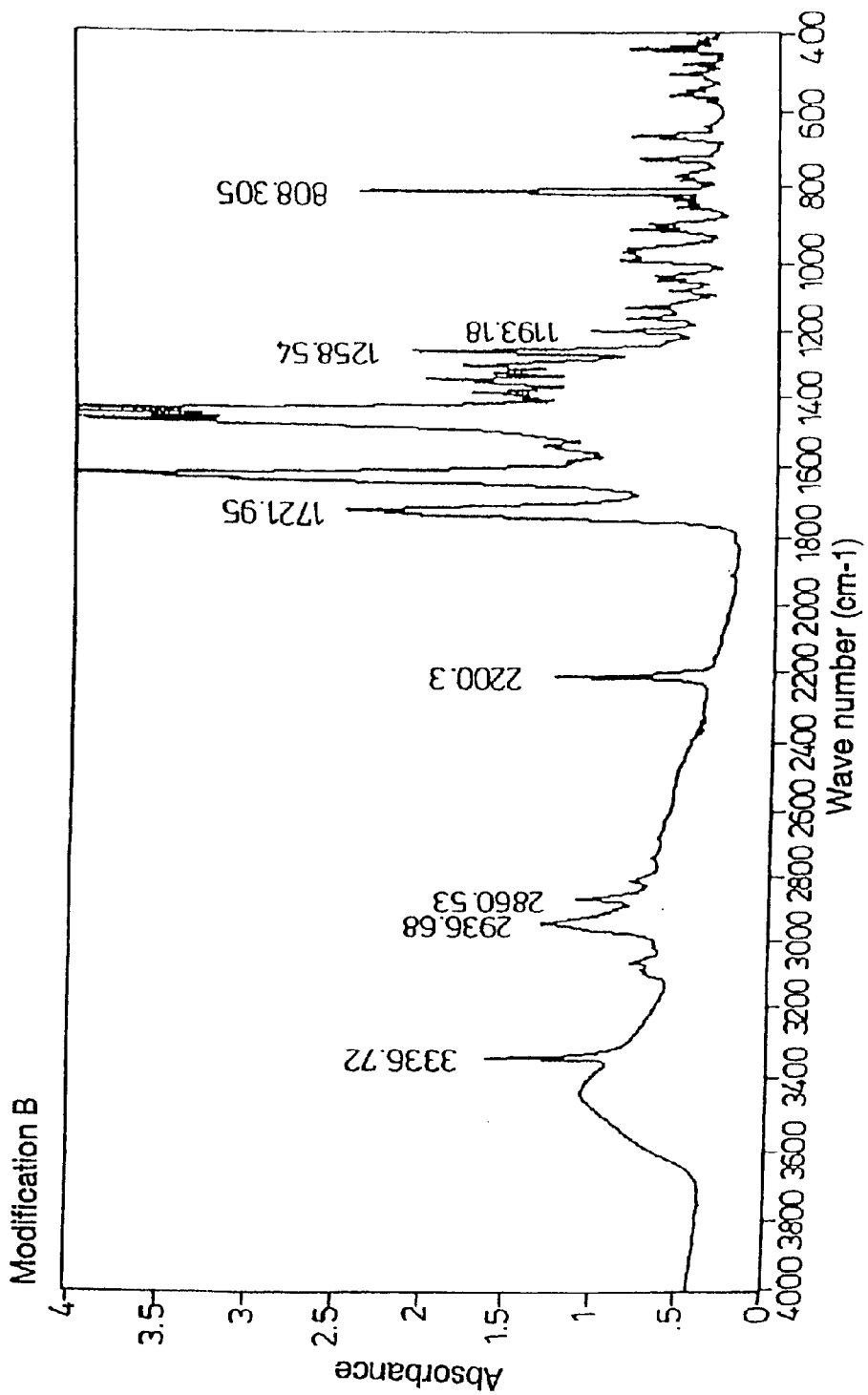

CCDC of the modification B is characterized in that it has an infrared spectrum, measured in KBr, as shown in FIG. 3.

CCDC of the modification B is characterized in that it is obtainable by one of the preparation processes given below. The crystal modification B of CCDC is obtained by reacting 7-halogeno-8-cyano-1-cyclopropyl-6-fluoro- 1,4-dihydro-4-oxo-3-quinolinecarboxylic acid of the formula (II)

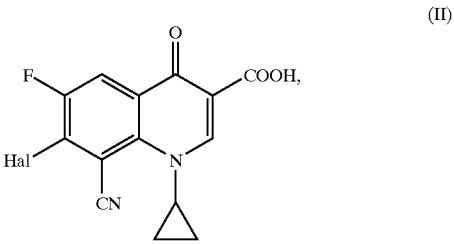

(II)

in which

Hal represents fluorine or, preferably, represents chlorine and (1S,6S)-2,8-diazabicyclo[4.3.0]nonane of the formula (III)

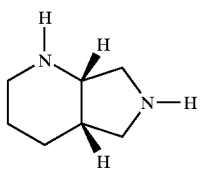

(III)

if appropriate in the presence of a base
in ethanol in a mixture with a polar aprotic diluent, such as N-methyl-pyrrolidone, dimethylformamide and sulpholane, or by heating CCDC of an unknown modification in a diluent, such as ethanol, propanol or isopropanol or in a mixture of these alcohols, with a polar aprotic diluent, such as N-methyl-pyrrolidone, dimethylformamide or sulpholane, if appropriate in the presence of a base, subsequently cooling the mixture and isolating CCDC of the crystal modification B.

CCDC of the crystal modification B is surprisingly stable and does not change into another crystal modification or the amorphous form, even on prolonged storage. In addition, compared with amorphous CCDC, the modification B tends to absorb less water from the atmosphere. For these reasons, it is highly suitable for preparing tablets or other solid formulations. Owing to its stability, it gives these formulations the desired long-lasting storage stability. Using the crystal modification B, it is therefore possible to prepare, in a defined and targeted manner, stable solid preparations of CCDC.

CCDC of the crystal modification B is highly active against pathogenic bacteria in the area of human or veterinary medicine. Its broad area of use corresponds to that of CCDC.

Preferred bases for preparing CCDC of the modification B are the tertiary amines trimethylamine, triethylamine, ethyldiisopropylamine (Hünig base), N-methyl-piperidine, N-ethyl-piperidine, N-propyl-piperidine and N-butyl-piperidine. Very particular preference is given to triethylamine and ethyl-diisopropylamine. From 1 to 2 mol of base, preferably from 1.1 to 1.5 mol, are usually employed per mole of the compound (II).

If a mixture of ethanol and N-methyl-pyrrolidone, dimethylformamide and sulpholane is used, ethanol and polar aprotic solvent are present in ratios of from 0.5 to 1 to 4 to 1; preference is given to ratios of from 1 to 1 to 3 to 1.

The reaction is carried out at atmospheric pressure or at elevated pressure between 1 bar and 100 bar, preferably between 1 bar and 20 bar.

The reaction is carried out at temperatures between 0° C. and 200° C., preferably between 20° C. and 150° C.

From 1 to 2 mol, preferably from 1 to 1.5 mol, of the compound (III) are usually employed per mole of the compound (II).

CCDC of the crystal modification B precipitates from the reaction mixture and can be filtered off with suction. The solid which has been filtered off with suction can be purified by washing with ethanol.

The starting materials of the formulae (II) and (III) for preparing CCDC are known (cf. DE-A 19 633 805).

If CCDC of an unknown modification is heated for a plurality of hours in a diluent such as ethanol, propanol or isopropanol or in a mixture of these alcohols with a polar aprotic diluent such as N-methyl-pyrrolidone, dimethylformamide or sulpholane, it is subsequently filtered off with suction at room temperature, washed with ethanol and then dried. In this procedure, it is likewise preferred to add triethylamine or ethyl-diisopropylamine as base (approximately 0.01 to 0.1 mol of base per mole of active compound).

The X-ray powder diffractogram for characterizing the crystal modification B of CCDC was obtained using a transmission diffractometer STADI-P with a location-sensitive detector (PSD2) from Stoe.

The melting point of the differential thermoanalysis was obtained using the DSC 820 unit from Mettler-Toledo. Here, the sample of CCDC of the crystal modification B was heated exposed to the atmosphere in an aluminium crucible at 10 K/min. The KBr IR spectrum was obtained using the FTS 60A unit from Biorad.

The examples below illustrate the invention without limiting it. The solvent/base systems used in the examples below are particularly preferred.

COMPARATIVE EXAMPLE

A mixture of 3.07 g of 7-chloro-8-cyano-1-cyclopropyl-6-fluoro-1,4-dihydro-4-oxo-3-quinolinecarboxylic acid, 1.39 g of (1S,6S)-2,8-diazabicyclo[4.3.0]nonane, 2.24 g of 1,4-diazabicyclo[2.2.2]octane (DABCO), 29.5 ml dimethylformamide and 29.5 ml of acetonitrile is stirred at room temperature for 16 hours. The reaction mixture is concentrated at a bath temperature of 60° C. using a rotary evaporator, and the residue is taken up in 10 ml of water. The resulting solution Is adjusted to pH 7 using dilute hydrochloric acid, and the solid is filtered off. The filtrate is extracted three times using 20 ml of dichloromethane each time. The organic phase is dried over sodium sulphate and filtered and the filtrate is concentrated at a bath temperature of 60° C. using a rotary evaporator. This gives 2.4 g of a light-brown solid which has the X-ray powder diffractogram shown in FIG. 4 and is therefore predominantly amorphous.

At a relative atmospheric humidity of 95% (established using a saturated solution of $Na_2HPO_4 \times 12\ H_2O$ with sediment in water), the solid obtained according to this procedure absorbs approximately 17% by weight of water within one day.

EXAMPLE 1

1012 g of 7-chloro-8-cyano-1-cyclopropyl-6-fluoro-1,4-dihydro-4-oxo-3-quinolinecarboxylic acid are initially charged in a mixture of 3300 ml of ethanol, 1980 ml of N-methyl-pyrrolidone and 534 g of diisopropylethylamine (Hünig base). The mixture is heated to reflux, and 459 g of (1S,6S)-2,8-diazabicyclo[4.3.0]nonane are then added dropwise. After the dropwise addition has ended, the mixture is stirred under reflux for another 3 hours and then allowed to cool to room temperature, and the solid is filtered off with suction and washed with a total of 1800 ml of ethanol.

Figure 1:
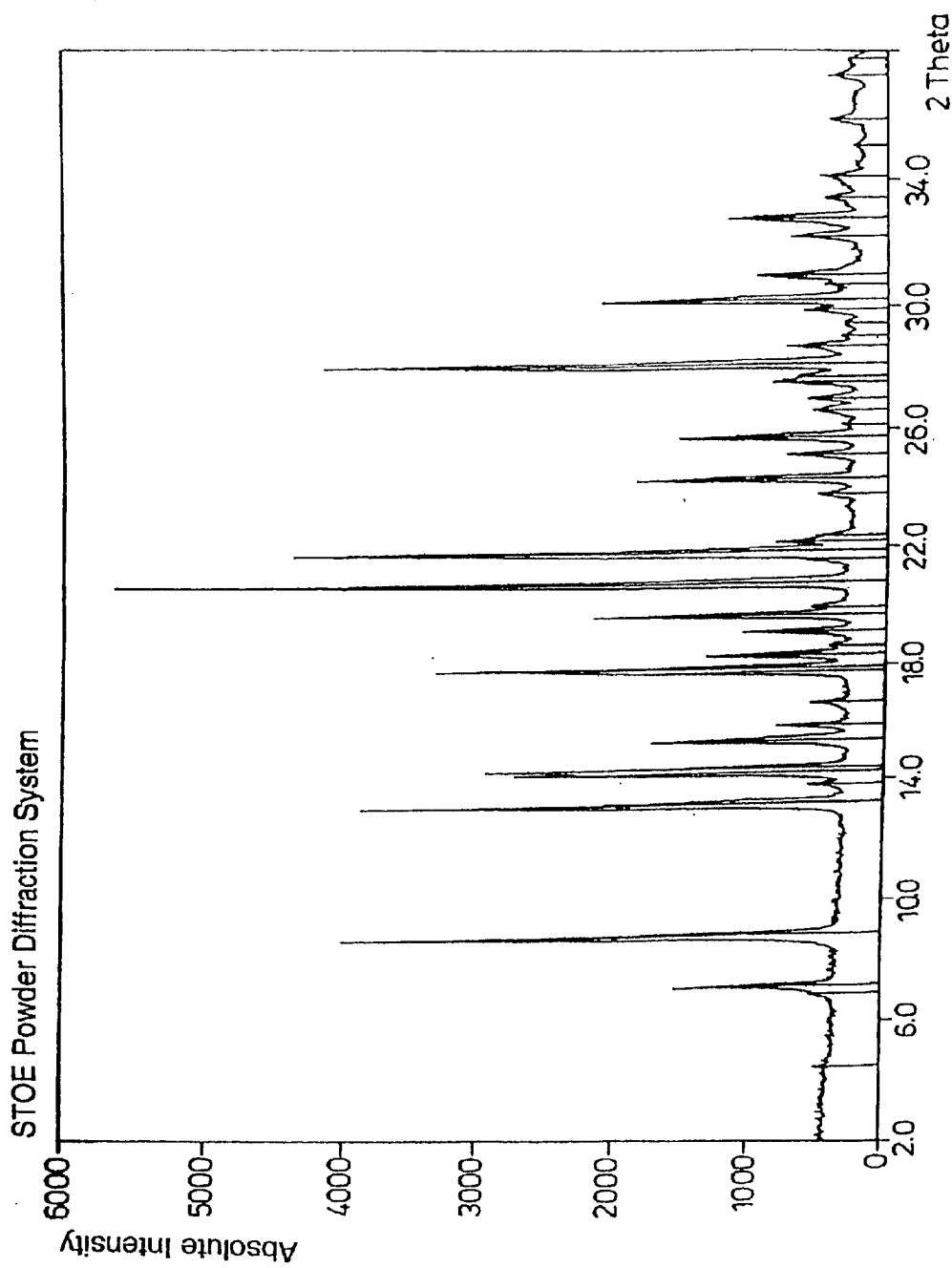

The resulting solid is suspended in a mixture of 4650 ml of ethanol and 41 g of Hünig base, and the reaction mixture is heated under reflux for 3 hours. The reaction mixture is allowed to cool again to room temperature, and the solid is filtered off with suction, washed with a total of 1000 ml of EtOH and dried at from 60 to 70° C. in a vacuum drying cabinet until the weight remains constant. This gives 1130 g of a beige solid which has the X-ray powder diffractogram shown in FIG. 1, the differential thermodiagram shown in FIG. 2 and the IR spectrum shown in FIG. 3.

At a relative atmospheric humidity of 95% (established using a saturated solution of $Na_2HPO_4 \times 12\ H_2O$ with sediment in water), the solid obtained according to this procedure absorbs approximately 1% by weight of water within one day.

EXAMPLE 2

A mixture of 4.6 g of 7-chloro-8-cyano-1-cyclopropyl-6-fluoro-1,4-dihydro-4-oxo-3-quinolinecarboxylic acid, 15 ml of ethanol, 9 ml of N-methyl-pyrrolidine and 1.9 g of triethylamine is heated to reflux. 2.08 g of (1S,6S)-2,8-diazabicyclo[4.3.0]nonane are added dropwise, and the mixture is then stirred under reflux for 3 hours. At room temperature, the solid is filtered off with suction, washed with a total of 10 ml of ethanol and dried until the weight remains constant. This gives 5.23 g of a beige solid whose differential thermodiagram corresponds to that of the modification B.

EXAMPLE 3

A mixture of 4.6 g of 7-chloro-8-cyano-1-cyclopropyl-6-fluoro-1,4-dihydro-4-oxo-3-quinolinecarboxylic acid, 15 ml of ethanol, 9 ml of N-methyl-pyrrolidine and 2.12 g of N-ethyl-piperidine is heated to reflux. 2.08 g of (1S,6S)-2,8-diazabicyclo[4.3.0]nonane are added dropwise, and the mixture is then stirred under reflux for 3 hours. At room temperature, the solid is filtered off with suction, washed with a total of 10 ml of ethanol and dried until the weight remains constant. This gives 5.1 g of a beige solid whose differential thermodiagram corresponds to that of the modification B.

EXAMPLE 4

A mixture of 9.2 g of 7-chloro-8-cyano-1-cyclopropyl-6-fluoro-1,4-dihydro-4-oxo-3-quinolinecarboxylic acid, 30 ml of ethanol, 18 ml of dimethylformamide and 4.85 g of Hünig base is heated to reflux. 4.17 g of (1S,6S)-2,8-diazabicyclo-[4.3.0]nonane are added dropwise, and the mixture is then stirred under reflux for 3 hours. At room temperature, the solid is filtered off with suction, washed with a total of 20 ml of ethanol and dried until the weight remains constant. This gives 11 g of a beige solid whose differential thermodiagram corresponds to that of the modification B.

EXAMPLE 5

A mixture of 9.2 g of 7-chloro-8-cyano-1-cyclopropyl-6-fluoro-1,4-dihydro-4-oxo-3-quinolinecarboxylic acid, 30 ml of ethanol, 18 ml of sulpholane and 4.85 g of Hünig base is heated to reflux. 4.17 g of (1S,6S)-2,8-diazabicyclo[4.3.0]nonane are added dropwise, and the mixture is then stirred under reflux for 3 hours. At room temperature, the solid is filtered off with suction, washed with a total of 20 ml of ethanol and dried until the weight remains constant. This gives 10.8 g of a beige solid whose differential thermodiagram corresponds to that of the modification B.

EXAMPLE 6

0.5 g of the solid from the comparative example are suspended in 3ml of ethanol. The reaction mixture is heated at reflux for 3 hours and the solid is filtered off with suction at room temperature and dried. The X-ray powder diffractogram corresponds to that of the modification B.

What is claimed is:

1. 8-Cyano-1-cyclopropyl-7-(1S,6S-2,8-diazabicyclo[4.3.0]nonan-8-yl)-6-fluoro-1,4-dihydro-4-oxo-3-quinolinecarboxylic acid (CCDC) of the crystal modification B, having an X-ray powder diffractogram with the following reflection signals (2 theta) of high and medium intensity.

| 2θ (2 theta) |
|---|
| 8.91 |
| 13.23 |
| 14.26 |
| 14.40 |
| 15.34 |
| 17.88 |
| 19.70 |
| 20.78 |
| 21.86 |
| 28.13 |
| 30.20. |

2. 8-Cyano-1-cyclopropyl-7-(1S,6S-2,8-diazabicyclo[4.3.0]nonan-8-yl)-6-fluoro-1,4-dihydro-4-oxo-3-quinolinecarboxylic acid (CCDC) of the crystal modification B of claim 1, obtained by reacting 7-halogeno-8-cyano-1-cyclopropyl-6-fluoro-1,4-dihydro-4-oxo-3-quinolinecarboxylic acid of the formula (II)

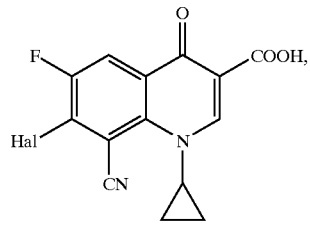

(II)

in which

Hal represents fluorine or chlorine and (1S,6S)-2,8-diazabicyclo[4.3.0]nonane of the formula (III)

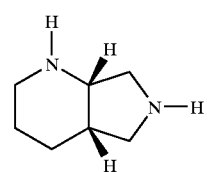

(III)

optionally in the presence of a base
in ethanol in a mixture with a polar aprotic diluent, selected from the group consisting of N-methyl-pyrrolidone, dimethylformamide and sulpholane;
or
by heating CCDC of an unknown modification in a diluent, which is ethanol, propanol or isopropanol or in a mixture of these alcohols, with a polar aprotic diluent which is N-methyl-pyrrolidone, dimethylformamide or sulpholane, optionally in the presence of a base, subsequently cooling the mixture and isolating CCDC of the crystal modification B.

3. Process for preparing CCDC of the modification B according to claim 1, comprising reacting 7-halogeno-8-cyano-1-cyclopropyl-6-fluoro-1,4-dihydro-4-oxo-3-quinolinecarboxylic acid of the formula (II)

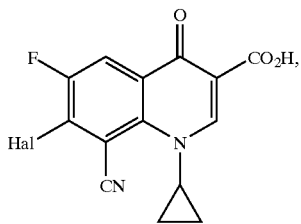

in which

Hal represents fluorine or chlorine and (1S,6S)-2,8-diazabicyclo[4.3.0]nonane of the formula (III)

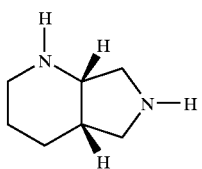

optionally in the presence of a base, in ethanol in a mixture with a polar aprotic diluent, which is selected from the group consisting of N-methyl-pyrrolidone, dimethylformamide and sulpholane, or heating CCDC of an unknown modification in a diluent, which is an alcohol selected from the group consisting of ethanol, propanol and an isopropanol or in a mixture of the alcohol, with a polar aprotic diluent, which is N-methyl-pyrrolidone, dimethylformamide or sulpholane, optionally in the presence of a base, subsequently cooling the resulting mixture and isolating CCDC of the crystal modification B.

4. Process for preparing CCDC of the modification B according to claim 3, wherein the solvent used is ethanol, and N-methyl-pyrrolidone, dimethylformamide or sulpholane is employed as a further solvent.

5. Process for preparing CCDC of the modification B according to claim 3, wherein the solvent used is ethanol, and N-methyl-pyrrolidone is employed as a further solvent.

6. Process for preparing CCDC of the modification B according to claim 4, wherein the base used is trimethylamine, triethylamine or ethyl-diisopropylamine.

7. A process for combating pathogenic bacteria comprising administering to a subject in need thereof an effective amount of CCDC of the modification B according to claim 1.

8. A process for combating pathogenic bacteria comprising administering to a subject in need thereof an effective amount of CCDC of the modification B according to claim 2.

9. The process of claim 3, wherein Hal in the compound of formula (II) is chlorine.

* * * * *